United States Patent
Lin

(10) Patent No.: US 8,877,169 B2
(45) Date of Patent: Nov. 4, 2014

(54) METHOD OF PREPARING HYDROGEL STRUCTURE

(75) Inventor: Tsu-Tai Lin, Taipei (TW)

(73) Assignee: Compose Element Limited, Taipei (TW)

( * ) Notice: Subject to any disclaimer, the term of this patent is extended or adjusted under 35 U.S.C. 154(b) by 324 days.

(21) Appl. No.: 13/462,424

(22) Filed: May 2, 2012

(65) Prior Publication Data

US 2013/0052153 A1 Feb. 28, 2013

Related U.S. Application Data

(60) Provisional application No. 61/527,685, filed on Aug. 26, 2011.

(51) Int. Cl.

| | | |
|---|---|---|
| *A61K 31/795* | (2006.01) | |
| *A61P 31/00* | (2006.01) | |
| *A61K 31/785* | (2006.01) | |
| *B32B 37/12* | (2006.01) | |
| *B32B 38/04* | (2006.01) | |
| *B32B 37/02* | (2006.01) | |

(52) U.S. Cl.
CPC ............... *A61K 31/785* (2013.01); *B32B 37/02* (2013.01); *A61K 31/795* (2013.01); *B32B 2535/00* (2013.01); *B32B 2309/04* (2013.01); *B32B 2310/0831* (2013.01)
USPC ........................................ 424/78.06; 604/368

(58) Field of Classification Search
CPC .............................. A61F 13/534; A61L 15/60
USPC .................................. 604/368, 385.19; 521/64
See application file for complete search history.

(56) References Cited

U.S. PATENT DOCUMENTS

2009/0297587 A1  12/2009  Yang et al.

FOREIGN PATENT DOCUMENTS

| CN | 1562382 A | 1/2005 |
|---|---|---|
| CN | 2008101224381 | 10/2008 |

OTHER PUBLICATIONS

CN Patent app No. 2008101224381 is also published as US2009297587A1.

*Primary Examiner* — Walter Webb
(74) *Attorney, Agent, or Firm* — WPAT, P.C.; Anthony King

(57) ABSTRACT

A method of preparing hydrogel structure, wherein the hydrogel structure comprises: (a) a one way penetrating polyurethane film layer, (b) a hydrophobic pressure sensitive adhesive layer, (c) a multi-directional elastic meltblown nonwoven, (d) an interpenetrating polymer network, and (e) a hydrophilic hydrogel; and the method comprises: (i) coating the hydrogel in a form of solution on the meltblown nonwoven to form a product 1, (ii) UV curing the product 1 in step (i), forming a composite comprising a hydrogel layer on the top, an interpenetrating polymer network in the middle, and a meltblown non-woven layer on the bottom, wherein the interpenetrating polymer network is a mixture of the hydrogel and the meltblown non-woven, (iii) providing polyurethane film layer coated with pressure sensitive adhesive layer, and (iv) laminating part of exposed fibers of meltblown non-woven with the pressure sensitive adhesive layer, forming a hydrogel structure.

13 Claims, 2 Drawing Sheets

METHOD OF PREPARING HYDROGEL STRUCTURE

FIELD OF THE INVENTION

The present invention relates to the field of medical dressing technology, specifically provides a hydrogel structure that can keep a suitable environment for wound healing, shorten the healing time, antiseptic and reduce the chances of being infected.

BACKGROUND OF THE INVENTION

According to recent scientific and statistical reports, the global trauma market is growing demand, especially in surgical trauma; the total people have exceeded 100 million per year and showed an upward trend year by year. People with trauma and lacerations caused by accidents are around 20 million per year. The number of burns is about 10 million people each year. People with ulcerative wounds caused by chronic diseases, diabetes and aging have been more than 30 million per year.

Because of the treatment needs and the popularity of endoscopic surgery, the risks caused by surgery have greatly reduced, but followed by the needs of better postoperative wound care and scar prevention. Currently there have been methods with the help of various advanced wound caring dressings, in order to shorten the healing time and eliminate scars.

The traditional dressings are made of natural plant fibers or animal hair materials such as gauze, cotton pad, wool, and all kinds of oiled gauzes. These dressings are only temporary covering materials that need to be replaced in a certain period of time. The study of wound dressings lets us grow scientific understanding of them. Studies have shown that: a better trauma dressing is to maintain a good environment for cell growth and healing at wound, to control and absorb exudates; breathable, moisture permeable and can prevent bacterial invasion; can closely stick to the surface of wounds; can carry and release the drug; also should have good tissue and blood compatibility that when taking it off from the wound surface, no adhesion and desquamation occurs; and also should have better mechanical properties and tensile strength, easy to use. In existing technology, such as published on Oct. 29, 2008 China patent application No. 200810122438.1 provided a preparation method for medical hydrogel bed dressing, and the patent published on Jan. 12, 2005 issue No. CN1562382A named "Water emulsion containing polyurethane-based hydrogel wound dressing and preparation method" is about a hydrogel as a base for medical dressing.

SUMMARY OF THE INVENTION

Figure 1:
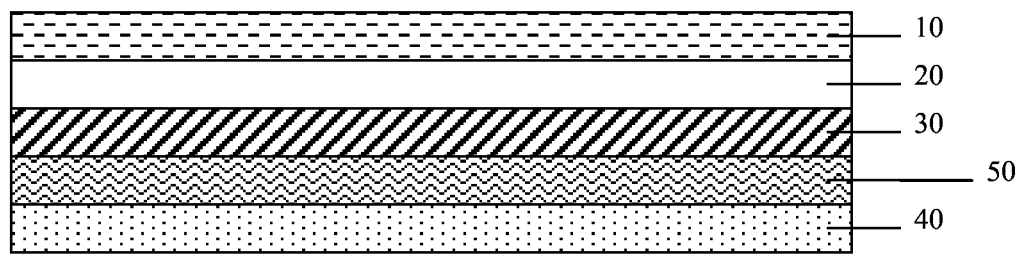
FIG. 1 is the schematic diagram of the hydrogel structure.
10 is the polyurethane film layer;
20 is the pressure sensitive adhesive layer;
30 is the meltblown nonwoven;
40 is the hydrogel;
50 is the interpenetrating polymer network.

The present invention relates to a method of preparing hydrogel structure, wherein the hydrogel structure comprises: (a) a one way penetrating polyurethane film layer, (b) a hydrophobic pressure sensitive adhesive layer, (c) a multi-directional elastic meltblown nonwoven, (d) an interpenetrating polymer network, and (e) a hydrophilic hydrogel; and the method comprises: (i) coating the hydrogel in a form of solution on the meltblown non-woven to form a product 1, (ii) UV curing the product 1 in step (i), forming a composite comprising a hydrogel layer on the top, an interpenetrating polymer network in the middle, and a meltblown non-woven layer on the bottom, wherein the interpenetrating polymer network is a mixture of the hydrogel and the meltblown non-woven, (iii) providing polyurethane film layer coated with pressure sensitive adhesive layer, and (iv) laminating part of exposed fibers of meltblown non-woven with the pressure sensitive adhesive layer, forming a hydrogel structure.

This invention also relates to a method of preparing hydrogel comprising: (a) mixing up acrylic amide monomer, acrylic solvent monomer, glycerol and photoinitiator to form a mixture I, (b) mixing up unsaturated double functional groups ester monomer and photoinitiator to form a mixture II, (c) stirring mixture I in step (a) and mixture II in step (b) to form a mixture III, and (d) laminating mixture III in step (c) to form hydrogel.

DETAILED DESCRIPTION OF THE INVENTION

The present invention provides a hydrogel structure for multiple traumas. The structure has better swollen properties; the surface stickiness changes based on the status of moisture aborting and can create the best healing environment. The hydrogel structure can give the wound dressing keeping a suitable environment for wound healing, shorten the healing time, antiseptic and reduce the chances of being infected.

Hence, the present invention provides a method of preparing hydrogel structure, wherein the hydrogel structure comprises: (a) a one way penetrating polyurethane film layer, (b) a hydrophobic pressure sensitive adhesive layer, (c) a multi-directional elastic meltblown nonwoven, (d) an interpenetrating polymer network, and (e) a hydrophilic hydrogel; and the method comprises: (i) coating the hydrogel in a form of solution on the meltblown non-woven to form a product 1, (ii) UV curing the product 1 in step (i), forming a composite comprising a hydrogel layer on the top, an interpenetrating polymer network in the middle, and a meltblown non-woven layer on the bottom, wherein the interpenetrating polymer network is a mixture of the hydrogel and the meltblown non-woven, (iii) providing polyurethane film layer coated with pressure sensitive adhesive layer, and (iv) laminating part of exposed fibers of meltblown non-woven with the pressure sensitive adhesive layer, forming a hydrogel structure.

In one embodiment, the method further comprises cutting the composite in step (ii).

In another embodiment, the interpenetrating polymer network strengthens tension and adhesive ability for wound covering.

In still another embodiment, the hydrogel absorb excess moisture or wound tissue fluid to maintain proper skin moisture.

In still another embodiment, the hydrogel comprises: (a) a monomer; (b) a plasticizer; (c) a photoinitiator; (d) a cross-linking agent; and (e) a thickener.

In still another embodiment, the monomer is acrylic amide monomer or acrylic sulfonate monomer.

In still another embodiment, the acrylic sulfonate monomer provides the hydrogel antiseptic effect.

In still another embodiment, the plasticizer is glycerol.

In still another embodiment, the thickener is glycerol.

In still another embodiment, the glycerol provides the hydrogel flexibility and increases the hydrophilicity.

In still another embodiment, the photoinitiator generates free radical and completes polymerization under 1 to 50 seconds of UV light irradiating.

In still another embodiment, the cross-linking agents are esters with unsaturated double functional groups.

In still another embodiment, the weight ratios of the hydrogel are: 15 to 30 units of acrylic amide monomer; 10 to 50 units of acrylic sulfonate monomer; 15 to 45 units of glycerol; 0.01 to 0.1 units of photoinitiator; and 0.01 to 0.2 units of unsaturated double functional groups ester monomer.

The interpenetrating polymer network includes part of the elastic meltblown non-woven, therefore strengthens tension. In this case, while the polyurethane film achieves multi-directional elasticity for proper wound covering, the hydrogel remain unbroken because of the better tension.

The interpenetrating polymer network also strengthens adhesive ability. The hydrogel itself is easy to detach when absorbing liquid. However, since the interpenetrating polymer network includes part of the meltblown non-woven, better adhesion to skin is provided. As such, it avoids easy detachment which causes secondary damage.

The UV curing step could also be achieved by other oxygen related procedure.

The present invention further provides a method of preparing hydrogel comprising: (a) mixing up acrylic amide monomer, acrylic solvent monomer, glycerol and photoinitiator to form a mixture I, (b) mixing up unsaturated double functional groups ester monomer and photoinitiator to form a mixture II, (c) stirring mixture I in step (a) and mixture II in step (b) to form a mixture III, and (d) laminating mixture III in step (c) to form hydrogel.

In one embodiment, the hydrogel comprises: (a) a monomer; (b) a plasticizer; (c) a photoinitiator; (d) a cross-linking agent; and (e) a thickener.

In another embodiment, the monomer is acrylic amide monomer or acrylic sulfonate monomer.

In still another embodiment, the acrylic sulfonate monomer provides the hydrogel antiseptic effect.

In still another embodiment, the plasticizer is glycerol.

In still another embodiment, the thickener is glycerol.

In still another embodiment, the glycerol provides the hydrogel flexibility and increases the hydrophilicity.

In still another embodiment, the photoinitiator generates free radical and completes polymerization under 1 to 50 seconds of UV light irradiating.

In still another embodiment, the cross-linking agents are esters with unsaturated double functional groups.

In still another embodiment, the weight ratios of the hydrogel are: 15 to 30 units of acrylic amide monomer; 10 to 50 units of acrylic sulfonate monomer; 15 to 45 units of glycerol; 0.01 to 0.1 units of photoinitiator; and 0.01 to 0.2 units of unsaturated double functional groups ester monomer.

The multilayer functional hydrogel structure in the present invention is laminated by take-up device. The hydrogel of the present invention contacts with the trauma as the fitting surface of the wound, making the wound in the appropriate moist condition for accelerating healing. The moist healing environment is conducive to wound healing, if the wound dehydrates, the cells cannot survive. Although a variety of moist gauze or bandage can also provide a moist healing environment, the gauze or bandage type of dressings are required frequently change, making newly formed cells damaged easily, causing the wound second damage, and there is the risk of dehydration.

The hydrogel of the present invention has the water-absorbing and sticky reducing features, and causes less damage compared to normal moist gauze or bandage such as Vaseline gauze in changing the dressings. Its water absorption ratio gives it the best moist condition that meets the requirements for wound healing. It absorbs excess moisture, keeping skin in proper humidity, and has more loading capacity for medicine.

The polyurethane film layer of the present invention is a tension, waterproof, breathable one way penetrating membrane; it provides thermoplastic deformable elasticity and tensioning that meets various needs of the wound cover. Meanwhile, the polyurethane film layer provides waterproof, bacteria resistance, breathable and cooling effects for the wound.

The pressure sensitive adhesive layer of the present invention is a hydrophobic material coated on the polyurethane film layer, making it fit with the skin.

The present invention can be applied on all kinds of wound dressings, dressings for ring circumcision surgery, and electrode dressings.

The beneficial effects of the present invention are that the hydrogel structure can make trauma dressings that have multi-directional elasticity to meet the use for many wounds, providing a better environment for wound healing, shorten the healing time, antiseptic and reduce the chances of being infected.

The following combined figures and specific implementing modalities that give the present invention further elaborations.

EXAMPLES

The examples below are non-limiting and are merely representative of various aspects and features of the present invention.

Example 1

The Method of Preparing Hydrogel Structure

Figure 2:
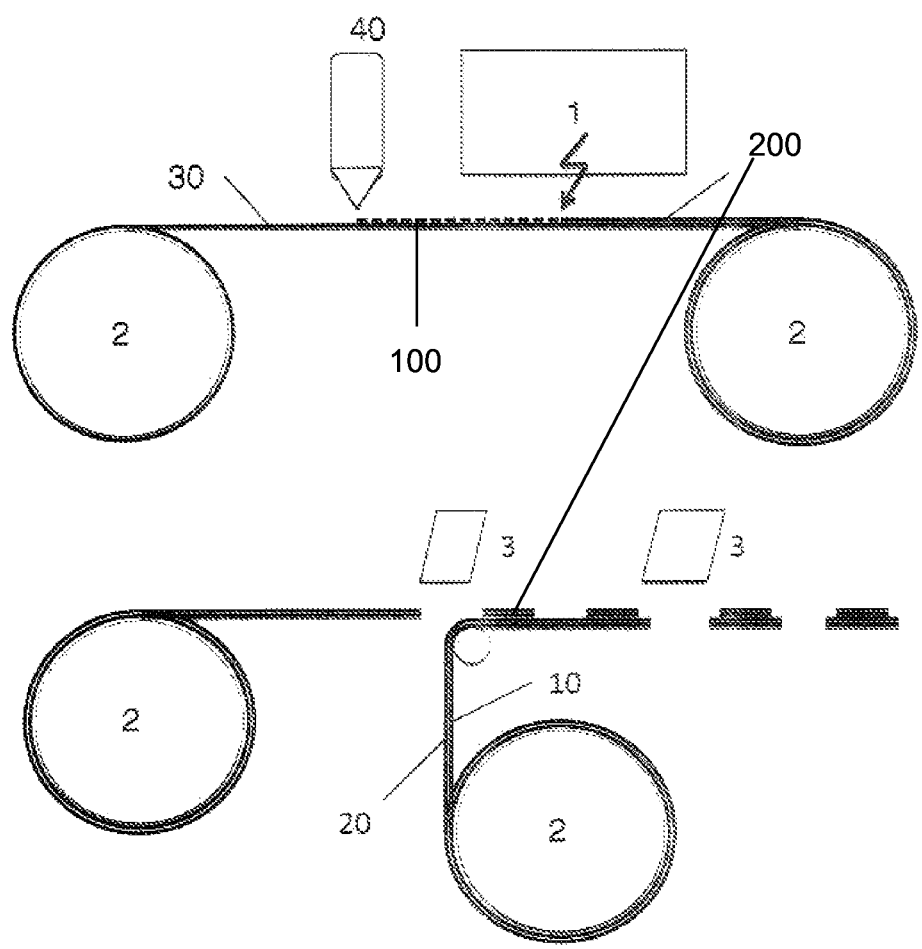
FIG. 2 is the schematic diagram of the method of preparing hydrogel structure.
1 is the UV light;
2 is the take-up device;
3 is the cutting tool;
10 is the polyurethane film layer;
20 is the pressure sensitive adhesive layer;
30 is the meltblown nonwoven;
40 is the hydrogel;
100 is the product 1;
200 is the composite comprising a hydrogel layer on the top, an interpenetrating polymer network in the middle, and a meltblown non-woven layer on the bottom.

As shown in FIG. 1, multilayer of the hydrogel structure comprising: polyurethane film layer (10), pressure sensitive adhesive layer (20), interpenetrating polymer network (50) which includes part of meltblown nonwoven (30) and hydrogel (40). FIG. 2 shows the method of preparing hydrogel structure, comprising: (i) Coating the hydrogel (40) in a form of solution on the meltblown non-woven (30) to form a product 1 (100) by take-up device (2), (ii) UV curing the product 1 (100) in step (i) by UV light (1), forming a composite (200) comprising a hydrogel (40) layer on the top, an interpenetrating polymer network (50) in the middle, and a meltblown non-woven (30) layer on the bottom, wherein the interpenetrating polymer network is a mixture of the hydrogel (40) and the meltblown non-woven (30), (iii) cutting and slitting the composite (200) in step (ii) by cutting tool (3), (iv) Providing polyurethane film layer (10) coated with pressure sensitive adhesive layer (20), and (v) Laminating part of exposed fiber of meltblown non-woven (30) with the pressure sensitive adhesive layer (20), forming a hydrogel structure.

Example 2

The Hydrogel Formulation

The hydrogel was made by the steps as follows:
(a) providing a mixture comprising: (I) mixing the photoinitiator and the acrylic amide monomer to dissolve; (II) adding glycerol and mix to dissolve; (III) adding acrylic sulfonate monomer and mix to dissolve; (IV) adding glycerol and mix up.
(b) further providing a mixture comprising: (I) mixing the photoinitiator and the unsaturated double functional groups ester monomer.
(c) mixing up the mixture of step (a) and step (b).
(d) crosslinked polymerizing the mixture of step (c) by irradiating UV light to form the hydrogel.
The weight ratios of the above were

| | |
|---|---|
| Acrylic amide monomer | 15 to 30 units |
| Acrylic sulfonate monomer | 10 to 50 units |
| Glycerol | 15 to 45 units |
| Photoinitiator | 0.01 to 0.1 units |
| Unsaturated double functional groups ester monomer | 0.01 to 0.2 units |

What is claimed is:

1. A method of preparing hydrogel structure, wherein the hydrogel structure comprises:
    (a) a one way penetrating polyurethane film layer,
    (b) a hydrophobic pressure sensitive adhesive layer,
    (c) a multi-directional elastic meltblown nonwoven,
    (d) an interpenetrating polymer network, and
    (e) a hydrophilic hydrogel;
    and the method comprises:
    (i) coating the hydrogel in a form of solution on the meltblown non-woven to form a product 1,
    (ii) UV curing the product 1 in step (i), forming a composite comprising a hydrogel layer on the top, an interpenetrating polymer network in the middle, and a meltblown non-woven layer on the bottom, wherein the interpenetrating polymer network is a mixture of the hydrogel and the meltblown non-woven,
    (iii) providing polyurethane film layer coated with pressure sensitive adhesive layer, and
    (iv) laminating part of exposed fibers of meltblown non-woven with the pressure sensitive adhesive layer, forming a hydrogel structure.

2. The method of claim 1, further comprises cutting the composite in step (ii).

3. The method of claim 1, wherein the interpenetrating polymer network strengthens tension and adhesive ability for wound covering.

4. The method of claim 1, wherein the hydrogel absorb excess moisture or wound tissue fluid to maintain proper skin moisture.

5. The method of claim 1, wherein the hydrogel comprises:
    (a) a monomer;
    (b) a plasticizer;
    (c) a photoinitiator;
    (d) a cross-linking agent; and
    (e) a thickener.

6. The method of claim 5, wherein the monomer is acrylic amide monomer or acrylic sulfonate monomer.

7. The method of claim 6, wherein the acrylic sulfonate monomer provides the hydrogel antiseptic effect.

8. The method of claim 5, wherein the plasticizer is glycerol.

9. The method of claim 5, wherein the thickener is glycerol.

10. The method of claim 8, wherein the glycerol provides the hydrogel flexibility and increases the hydrophilicity.

11. The method of claim 5, wherein the photoinitiator generates free radical and completes polymerization under 1 to 50 seconds of UV light irradiating.

12. The method of claim 5, wherein the cross-linking agents are esters with unsaturated double functional groups.

13. The method of claim 5, wherein posses weight ratios of the hydrogel are:

| | |
|---|---|
| Acrylic amide monomer | 15 to 30 units |
| Acrylic sulfonate monomer | 10 to 50 units |
| Glycerol | 15 to 45 units |
| Photoinitiator | 0.01 to 0.1 units |
| Unsaturated double functional groups ester monomer | 0.01 to 0.2 units. |

* * * * *